United States Patent [19]

Nelson

[11] 4,044,147
[45] Aug. 23, 1977

[54] N-(ACYL)-p-AMINO-N'-(MONOSUB-STITUTED)-BENZAMIDE ANTI-ULCER AGENTS

[75] Inventor: Albin J. Nelson, Ledyard, Conn.

[73] Assignee: Pfizer Inc., New York, N.Y.

[21] Appl. No.: 690,300

[22] Filed: May 26, 1976

[51] Int. Cl.² .................. A61K 31/24; A61K 31/19; C07C 101/44
[52] U.S. Cl. .................. 424/309; 260/295 AM; 260/471 A; 260/506; 260/518 R; 260/558 A; 260/332.2 C; 424/263; 424/275; 424/303; 424/317; 424/320
[58] Field of Search .................. 424/309, 317; 260/471 A, 518

[56] References Cited

U.S. PATENT DOCUMENTS 3,780,090  12/1973  Akiba et al. .................. 260/471 A

OTHER PUBLICATIONS

Moriyama et al., Chemical Abstracts 78: 29487k, (1973).
Torihara et al., Chemical Abstracts 84: 179900c, (1976).

Primary Examiner—Norman A. Drezin
Attorney, Agent, or Firm—Connolly and Hutz

[57] ABSTRACT

The preparation of novel N-(acyl)-p-amino-N'-(monosubstituted) benzamides by modified Schotten-Baumann reaction of the corresponding p-aminobenzamides is described. These compounds are effective anti-ulcer agents.

10 Claims, No Drawings

N-(ACYL)-P-AMINO-N'-(MONOSUBSTITUTED)-BENZAMIDE ANTI-ULCER AGENTS

BACKGROUND OF THE INVENTION

This invention relates to novel N-(acyl)-p-amino-N'-(mono-substituted) benzamides and to their use as anti-ulcer agents.

Chronic gastric and duodenal ulcers, collectively known as peptic ulcers, are a common ailment for which a variety of treatments have been developed. The treatment depends upon the severity of the ulcer and ranges in scope from simple dietary measures to medicinal or drug treatment and surgery.

Peptic ulcer management by drug therapy has received significant attention recently and most of the drugs which have been developed avoid the anti-cholinergic approach inherent in atropine derivatives because of that approach's undesirable side effects such as tachycardia, dry mouth and diarrhea. ("The Pharmacological Basis of Therapeutics," L. S. Goodman and A. Gilman, Eds. Macmillan, New York 1970). Some examples of these recently developed drugs are glycyrrhetinic acid derivatives (U.S. Pat. No. 3,891,750) and antisecretory compounds such as phenoxy pyrimidines (U.S. Pat. No. 3,862,190).

One of the most widely acclaimed anti-ulcer agents used for treatment is the glycyrrhetinic acid derivative, carbenoxolone sodium ("Carbenoxolone Sodium: a symposium," J. M. Robinson and F. M. Sullivan, Eds., Butterworth, London, 1968). It has been reported to prevent formation and to promote healing of gastric ulcers in animal models and has been shown to promote healing in controlled clinical trials. Carbenoxolone sodium has been prescribed for ulcer sufferers by European general practitioners and is a derivative of the essence of the European folk remedy (licorice) for ulcers. It is, however, not without its untoward side effects, which result from its similarity in pharmacology and structural features to adrenocorticosteroids (J. Groen, et al., Acta, Med. Scand. Suppl., 312, 745 (1956)). These aldosterone-like properties include such effects as anti-diuresis, potassium loss and muscle wasting, and obviously detract from carbenoxolone's benefaction.

From a search to find anti-ulcer compounds having selective carbenoxolone characteristics, it has been surprisingly discovered that N-(acyl)-p-amino-N'-(monosubstituted) benzamides have carbenoxolone-like anti-ulcer activity in animal models.

SUMMARY OF THE INVENTION

The present invention comprises novel and effective antiulcer agents having the N-(acyl)-p-amino-N'-(monosubstituted) benzamide formula below:

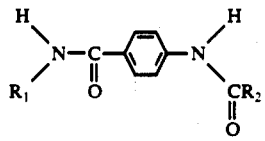

wherein:

$R_1$ is selected from the group consisting of n-alkyl having from seven to eighteen carbon atoms, phenyl, benzyl, phenylethyl, and α-pyridyl;

$R_2$ is selected from the group consisting of alkyl having from one to six carbon atoms, —$(CH_2)_nCO_2R_3$, —(-CHOR$_4$)$_n$CO$_2$R$_3$, —(CH$_2$)$_v$SO$_3$H, naphthyl, biphenyl, phenylethyl, benzyl, phenoxy, pyridyl, α-theinyl and

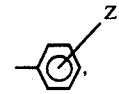

said Z substituent being selected from the group consisting of hydrogen, halogen, alkyl having from one to four carbon atoms, —$CH_3$, —$OR_5$, —$(CH_2)_uCO_2R_3$ and —$(CH_2)_uCONH_2$;

$R_3$ is hydrogen or alkyl having from one to five carbon atoms;

$R_4$ is hydrogen or acetyl;

$R_5$ is hydrogen or alkyl having from one to three carbon atoms;

$n$ is an integer from one to four;

$u$ is an integer from zero to two;

$v$ is an integer from two to four;

and the alkali, alkaline earth and ammonium salts of those compounds having at least one carboxylate group.

Of interest are several embodiments of the present invention wherein $R_1$ is n-alkyl having from seven to eighteen carbon atoms and which exhibit high activity in anti-ulcer therapy.

Of even more interest are those compounds wherein $R_1$ is n-alkyl having from seven to eighteen carbon atoms and $R_2$ is

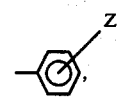

pyridyl or -$(CH_2)_nCO_2R_3$.

Of most interest are N-(3-carboxypropionyl)-p-amino-N'-(decyl) benzamide and N-(benzoyl)-p-amino-N'-(tridecyl) benzamide which exhibit particularly high activity in anti-ulcer therapy.

DETAILED DESCRIPTION OF THE INVENTION

The novel compounds described in the formula above comprise the products of this invention and are prepared by contacting a p-amino-N-(monostubstituted) benzamide of the formula with

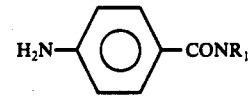

where $R_1$ is defined as above, an acylating reagent selected from the group consisting of

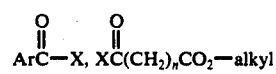

having from one to five carbon atoms in the alkyl group,

having from one to five carbon atoms in the alkyl group,

and

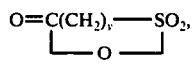

Ar being selected from the group consisting of naphthyl, biphenyl, phenylethyl, benzyl, phenoxy, pyridyl, α-thienyl and

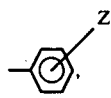

said Z substituent being selected from the group consisting of hydrogen, halogen, alkyl having from one to four carbon atoms, $-CF_3$, $-OR_5$, $-(CH_2)_uCO_2$-alkyl having from one to five carbon atoms in the alkyl group, and $-(CH_2)_uCONH_2$;

$R_5$, $n$, $u$, $v$ and $y$ being defined as above;

and X being selected from the group consisting of alkoxycarboxy having from one to four carbon atoms in the alkoxy group, imidazol-1-yl, t-butyl carboxy, Br, I and especially Cl.

Several preliminary steps are appropriate for the preparation of the p-amino-N-(monosubstituted) benzamide which is acylated in the above process. These steps and the acylation step together form the complete synthetic pathway to the novel products of the invention as is illustrated by Scheme A.

Scheme A

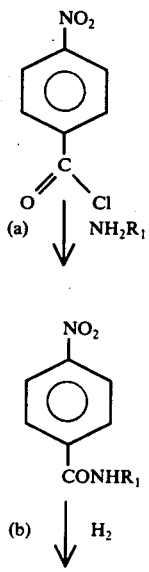

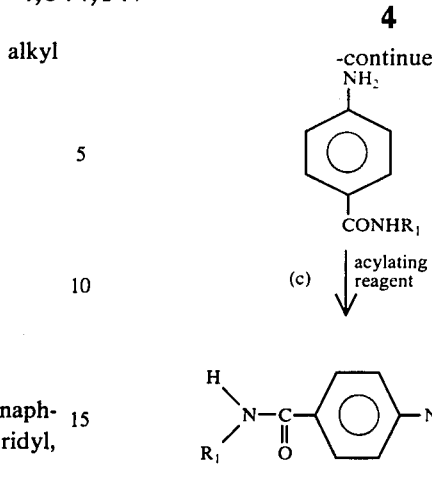

In Scheme A, step (a) is a Schotten-Baumann reaction of p-nitro benzoyl chloride 1 with a primary amine $R_1HN_2$, $R_1$ being defined as above;

step (b) is a reduction of the nitro group of 2 by hydrogen and catalyst methods or by metal in acidic media methods;

and step (c) is a Schotten-Baumann reaction of the p-amino benzamide 3 with the previously defined acylating reagent.

According to reaction scheme A, the p-amino-N-(monosubstituted) benzamide starting material 3, is prepared by reduction (step b) of the p-nitrobenzamide 2 which in turn is prepared by reaction (step a) of p-nitrobenzoyl chloride with the desired primary amine. The conditions applied to the reaction of step (a) are usually those of the Schotten-Baumann method which is the combination of aqueous alkali and an organic solvent, usually benzene, chloroform, toluene or methylene chloride, to form a two phase system. Other conditions which are equally successful in completing this reaction consist of a one-phase organic-base, organic-solvent combination wherein the organic base is usually pyridine or triethylamine.

Catalytic hydrogenation is the usual method employed in reduction step (b) and is conducted by known methods. The catalyst can be chosen from the multitude available and appropriate for reduction of a nitro group, some of these catalysts being platinum oxide, Raney nickel and palladium on charcoal. Alternatively the desired p-amino benzamide, 3 can be synthesized by metal reduction of intermediate 2, that is, p-nitro-N-(monosubstituted) benzamide, in acidic media, according to the procedure of H. Wenker, *J. Am. Chem. Soc.,* 60, 1081 (1938). A multitude of transition metals and reductive salts can be used for the reduction of the nitro group such as iron in acetic acid, stannous chloride in hydrochloric acid and zinc in acetic acid. The most convenient and preferred procedure of those which can be employed for reduction of the nitro group is catalytic reduction over platinum oxide (Adam's catalyst).

The choice of the primary amine, $R_1NH_2$, is dictated by the structure of the desired final product. For example, when the final product 4 desired is N-(benzoyl)-p-amino-N'-(n-decyl) benzamide, the primary amine will be n-decyl amine and the intermediate 3 will be p-amino-N'-(n-decyl) benzamide.

The last step of Scheme A, reaction step (c) which produces the products of the invention, is most conveniently conducted by modifying the classic two-phase Schotten-Baumann procedure for amide formation, by employing liquid or solid organic amine and desirable tertiary amines such as pyridine, triethylamine and lutidine instead of the more conventional aqueous alkali, thereby achieving a one phase solution with the inert, hydrophobic organic solvent. For example, a solution of benzoyl chloride in a dry, inert organic solvent such as benzene or chloroform is dropwise added to a stirring solution of p-amino-N-(n-decyl) benzamide in an organic base, solvent mixture usually consisting of benzene or chloroform and pyridine or triethylamine at room temperature. The reaction usually starts immediately, as evidenced by the partial precipitation of pyridinium hydrochloride, and a typical procedure will consist of refluxing the reaction mixture for a period of one to five hours or until the formation of N-(benzoyl)-p-amino-N'-(n-decyl) benzamide is substantially complete.

The reaction mixture is then cooled and, if desired, it can be diluted with benzene or other hydrophobic organic solvent such as ethyl acetate, chloroform or methylene chloride in anticipation of water extraction. In either case, the usual workup procedure which follows consists of extraction of the reaction mixture with water, drying the organic phase, e.g., with a hydrophilic inorganic salt such as magnesium sulfate, and removal of the organic solvent from the filtered organic solution by evaporation in vacuum. Final purification of the resulting crude product is usually achieved by recrystallization from an organic solvent such as ethanol, methanol, ethanol/benzene or ethanol/water. Other procedures that can be used to purify and isolate product from more complex reaction mixtures include column chromatography, vacuum distillation and high pressure liquid chromatography.

The acylating reagent, which is the reagent of step (c), is readily available or easily prepared by known methods. For instance, contacting the aromatic carboxylic acid $ArCO_2H$ (wherein Ar is defined as above) with thionyl chloride under dry conditions at room temperature for a short time until the reaction is substantially complete will generate the member of the acylating reagent group, ArCOCl. The usual isolation procedure for this type of reagent, e.g., carboxylic acid halides, calls for removal of the excess thionyl chloride, commonly by vacuum evaporation, followed by triturating the resulting crude acid chloride with an inert organic solvent. This so-treated carboxylic acid halide then can be used as such in its unpurified state as the acylating reagent of the Schotten-Baumann reaction to produce the products of the invention. Other methods to make carboxylic acid halides are appropriate here and include such methods as treatment of the desired carboxylic acid with the appropriate oxalyl halide, $PCl_3$ or $PCl_5$.

The leaving group of the acylating reagent described above is halogen, e.g., the acylating reagent is an acid halide, but other leaving groups can be employed with equal facility as the X of the acylating reagent. Mixed anhydrides and pseudohalogens such as imidazol-1-yl are both groups which when used as the leaving group X of the acylating reagent, will easily allow the acylation of the p-amino-N-(monosubstituted) benzamide using those common reaction conditions reported in the literature. For instance, methyl hydrogen glutarate can be contacted with ethyl chloroformate, isopropyl chloroformate or pivaloyl chloride in the presence of an inert organic solvent and organic amine to form an acylating reagent which is, in the case of ethyl chloroformate, the mixed anhydride $CH_3O_2C(CH_2)_3CO_2CO_2Et$. This mixed anhydride type of acylating reagent can then be used in the same manner as the carboxylic acid halide to acylate the p-amino-N-(monosubstituted) benzamide except that in this case the presence of an organic amine base is not necessary during the final acylation step.

The four types of carboxylic acid halides of the present invention being produced in the above manner are aromatic acid halides (ArCOX), aliphatic acid halides

w-carboxyalkylaliphatic carboxylic acid halides

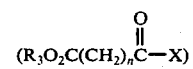

and ω-carboxyalkylhydroxyaliphatic carboxylic acid halides

wherein Ar, $R_3$, $R_4$, X, $n$ and $y$ are defined above. Of these types, the dicarboxylic acid derivatives, $R_3O_2C(CH_2)_nCOX$ and

are prepared by mixing thionyl chloride with the corresponding half acid, half ester compound, $R_3O_2C(CH_2)_nCO_2H$ or $R_3O_2C(CHOR_4)_nCO_2H$, which is made by disproportionating a stoichiometric mixture of the diacid and the diester. For instance, dimethyl succinate is disproportionated by succinic acid in a hot (120°-140°) solution of di-n-butyl ether and anhydrous HCl which produces, after purification, methyl hydrogen succinate in good yield. This succinate is then treated with thionyl chloride to produce the acid chloride. The hydroxy diacid derivatives, $R_3O_2C(CHOR_4)_nCOX$ or, for example, the acid chloride of monomethyl diacetyl tartarate, are prepared in the same manner but the hydroxyl groups must first be protected, usually as acetyl esters according to the procedure of H. J. Lucas and W. Baumgarden, *J. Am. Chem. Soc.*, 63, 1655 (1941).

The N-w-(sulfonoxyalkanoyl)-p-amino-N'-(monosubstituted) benzamide compounds of the present invention can be prepared by contacting the p-amino-N-(monosubstituted) benzamide with the member of the acylating reagent group which is the intramolecular anhydride of an w-sulfonoxyalkanoid acid wherein the alkanoic group is three, four or five carbons in length.

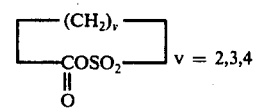

w-sulfoalkanoic anhydride

The novel products of this invention which result from step (c) reaction of an acylating reagent derived from an aliphatic acid, $C_yH_{2y+1}CO_2H$ wherein $y$ is as defined above, can also be prepared by contacting the p-amino-N-(monosubstituted) benzamide with an acylating reagent which is the appropriate aliphatic anhydride,

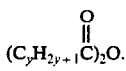

This procedure is usually accomplished by stirring the p-amino-N-(monosubstituted) benzamide with a large excess of the anhydride, for instance acetic or propionic anhydride, which also functions as the solvent.

The process of Scheme A is succinctly described as one which first forms the amide moiety and then forms the anilide moiety. A suitable alternate route entails the reversal of the above process namely, formation first of the anilide fragment and then formation of the amide moiety.

The alternate route process, illustrated by synthetic Scheme B, wherein $R_1$ and $R_2$ are each defined as above, employs alkyl-p-aminobenzoate, 5, having from one to four carbon atoms in the alkyl group and especially the methyl ester because of its ease of preparation and relative availability, as the starting material. The amino group of this benzoate is acylated, reaction step (d), with the appropriate acylating reagent and then the methyl carboxylate of the resulting p-carboxymethyl-N-monosubstituted anilide, 6, is hydrolyzed, reaction step (e), with dilute sodium bicarbonate to produce p-carboxy-N-(monosubstituted) anilide 7. This p-carboxyanilide, 7, is then stirred, reaction step (f) with thionyl chloride or other halogenating reagent to produce the corresponding carboxylic acid halide 8 which can then be contacted, reaction step (g), with the desired primary amine to produce the novel products 4 of the invention.

Scheme B

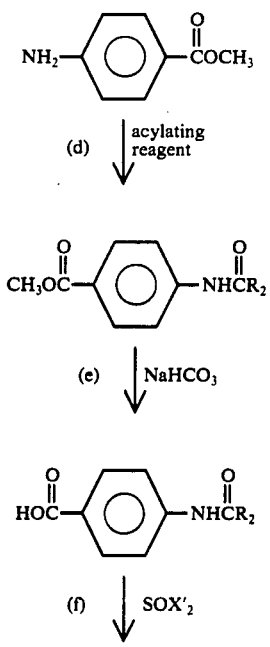

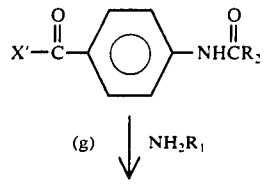

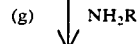

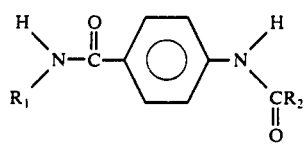

In Scheme B, step (d) is a Schotten-Baumann reaction of 5 with the appropriate acylating reagent which is the same as that defined in Scheme A above;

step (e) is alkaline hydrolysis of the ester;

step (f) is formation of the carboxylic acid halide 8 which can be accomplished by exposing the acid 7 to $PCl_3$, $PCl_5$, an oxalyl halide, or preferrably thionyl chloride;

step (g) is a Schotten-Baumann reaction of 8 with the appropriate amine $R_1NH_2$;

X' is halogen.

The conditions appropriate for the Schotten-Baumann reactions and the acid halide formation are as previously described. The alkaline hydrolysis is effected by stirring a mixture of the anilide 6, with a base such as sodium bicarbonate, sodium carbonate or dilute sodium or potassium hydroxide in aqueous alcohol such as methanol or ethanol until cleavage of the ester is essentially complete.

The compounds described herein are effective anti-ulcer agents and can be given by both the intraperitoneal and oral routes of administration to accelerate healing and prevent formation of gastric ulcers. Their anti-ulcer activity can be demonstrated in several animal models in which several known human anti-ulcer agents are also active. (W. E. Perkins, *Brit. J. Pharm.*, 47, 847, (1973)). Their use as control agents for gastric ulceration is appropriate in situations where ulceration has already occurred and also in situations were prophylactic treatment is warranted. Particularly valuable for ulcer treatment and prevention are the preferred compounds N-(3-carboxypropionyl)-p-amino-N'-(n-decyl) benzamide and N-(benzoyl)-p-amino-N'-(n-tridecyl) benzamide.

The valuable products of this invention can be administered alone or in combination with a pharmaceutical carrier selected on the basis of the chosen route of administration and standard pharmaceutical practice. For example, they can be administered orally in the form of tablets containing conventional excipients, binders and disintegrants, e.g., polyvinylpyrrolidone, sodium citrate, calcium carbonate and dicalcium phosphate, starch, alginic acid, complex silicates, milk sugar, gelatin and acadia.

Similar compositions may also be administered orally in gelatin capsules, the preferred excipients being lactose or milk sugar, as well as high molecular weight polyethylene glycols. These compounds can be formulated as elixirs or oral suspensions which may contain flavoring or coloring agents and may then also be used for oral administration to combat ulceration.

In general these anti-ulcer agents are ordinarily administered orally at dosage levels ranging from about 1.0 mg. to about 50 mg. per kg. of body weight per day, although variations will necessarily occur depending upon the condition and individual response of the subject being treated and the particular agent and type of pharmaceutical formulation chosen.

The activity of the compounds of the present invention, as anti-ulcer agents, is determined by their ability to inhibit ulcer formation in cold-restraint stressed rats according to the procedure described by H.-J. Hess, et al. in U.S. Pat. No. 3,891,750. This method essentially compares the median number of gastric erosions recorded in the control group with the median number of gastric erosions recorded in the drug-treated group and from this the percent reduction in the total number of lesions (%R.T.L.) can be readily calculated and reported as anti-ulcer activity per se.

Results thus obtained with several products of the present invention, when administered to non-fasted rats intraperitoneally at doses as low as 10 mg./kg., are presented below.

| Compound | Anti-ulcer Activity (%R.T.L.) | |
|---|---|---|
| | 10 mg/kg | 32 mg/kg |
| $CH_3CAr_1$  | 0 | 44 |
| $CH_3CAr_2$  | 68 | 63 |
| $PhCAr_1$  | 29 | — |
| $PhCAr_2$  | — | 100 |
| 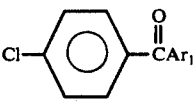 | — | 100 |
| 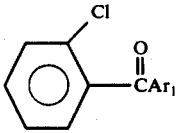 | — | 81 |
| 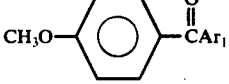 | 50 | 79 |
| 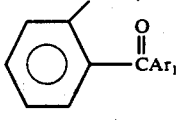 | — | 49 |
|  | 47 | 80 |

-continued

| Compound | Anti-ulcer Activity (%R.T.L.) | |
|---|---|---|
| | 10 mg/kg | 32 mg/kg |
| 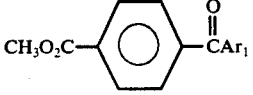 | — | 67 |
| 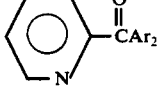 | — | 63 |
| 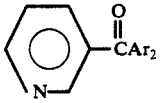 | — | 92 |
| 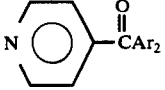 | — | 31 |
| $PhOCAr_2$  | 32 | 54 |
| $PhCH_2CAr_1$  | — | — |
| $CH_3O_2C(CH_2)_2COAr_1$ | 47 | 88 |
| $HO_2C(CH_2)_2COAr_1$ | 56 | 88 |
| $HO_3S(CH_2)_2COAr_1$ | — | 63 |
| $CH_3O_2C(CHOAc)_2COAr_1$ | — | 51 |
| $HO_2C(CHOH)_2COAr_1$ | — | 97 |
| Carbenoxolone Sodium | no protection | 80 |

$Ar_1$ is 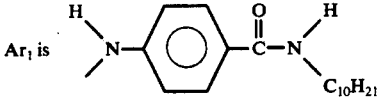

$Ar_2$ is 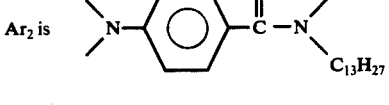

The avoidance of aldosterone-like anti-diuresis and anticholinergic activity by compounds of the present invention is represented by an example of one of the preferred compounds, N-(3-carboxypropionyl)-p-amino-N'-(decyl) benzamide A which produced an anti-ulcer activity of 58% R.T.L. when orally administered at a dose of 32 mg./kg. in the above described cold-restraint stressed rat model.

The ability of the compounds of the present invention and of carbenoxolone to cause or prevent diuresis was determined according to the method described by C. A. Lipinski in U.S. Pat. No. 3,891,750. The results obtained are presented below:

| Treatment | Test 1 Dose | Urine Output, ml. |
|---|---|---|
| Control (placebo) | — | 3.34 ± 1.61 |
| Benzamide A | 32 mg./kg. p.o. | 3.53 ± 0.88 |
| | Test 2 | |
| Control (placebo) | — | 2.45 ± 0.55 |
| Carbenoxolone sodium | 100 mg./kg. p.o. | 0.13 ± 0.11 |

Thus the compounds of the present invention have neither diuretic or anti-diuretic activity.

The presence or absence of anti-cholinergic activity in the biological profile of the compounds of the present invention was determined according to the procedure of M. M. Winbury, et al. in *J. Pharm. Exp. Therap.*, 95, 53 (1949). At a dose of 32 mg./kg. p.o. benzamide A did not protect the rats from the chromodacryorrhea (bloody lacrimation) produced by a 10 mg./kg. intraperitoneal dose of methacholine chloride. In this system 5 mg./kg. i.p. of atropine sulfate gave full protection for more than 80 minutes.

PREPARATION A

To a stirred solution consisting of 15.73 g. (0.10 mole) of n-decylamine dissolved in 200 ml. of chloroform at room temperature (~25° C), was added 18.5 g. (0.10 mole) of p-nitrobenzoyl chloride in the form of a solid material divided into separate small portions. Upon completion of this step, 250 ml. of 5% aqueous sodium hydroxide solution was rapidly added to the chloroform solution and the resulting two-phase reaction mixture was then stirred overnight (~16 hours) at room temperature. After separation of the two phases, the aqueous phase was washed once with 200 ml. of chloroform and this chloroform washing added to the organic phase. The combined organic solution was then washed once with 300 ml. of a saturated aqueous sodium chloride solution and finally dried over anhydrous magnesium sulfate. After removal of the drying agent by suction filtration and of the chloroform solvent by evaporation under reduced pressure, the resulting crude solid residue was recrystallized from a minimum amount of chloroform and methanol to give 20.82 g. (95%) of pure p-nitro-N-(n-decyl)benzamide (m.p. 88°–90° C.).

The following p-nitro-N-alkylbenzamides were prepared by the same procedure using an equivalent amount in moles of the appropriate monoalkylamine.

p-nitro-N-(n-octyl)benzamide, m.p. 82°–84° C.
p-nitro-N-(n-nonyl)benzamide, m.p. 79°–81° C.
p-nitro-N-(n-undecyl)benzamide, m.p. 88°–89° C.
p-nitro-N-(n-dodecyl)benzamide, m.p. 93°–94° C.
p-nitro-N-(n-tridecyl)benzamide, m.p. 85°–86° C.
p-nitro-N-(n-pentadecyl)benzamide, m.p. 95°–96° C.
p-nitro-N-(n-hexadecyl)benzamide, m.p. 96°–99° C.

n-Heptyl amine, benzylamine, β-phenylethylamine and α-pyridylamine can also be converted into the corresponding p-nitro-N-monosubstituted benzamides by the foregoing procedure.

PREPARATION B

A slurry of 29.00 g. (0.095 mole) of p-nitro-N-(n-decyl)benzamide in 200 ml. of methanol contained in a Parr shaker bottle was warmed slightly to dissolve all the benzamide. Adams platinum oxide catalyst (0.1 g.) was then added and the mixture placed on a Parr hydrogen reduction apparatus and shaken until no further hydrogen uptake could be detected (27.0 pounds of hydrogen was absorbed over a period of 0.67 hours). The resultant slurry was next removed from the reaction vessel and subsequently dissolved in 250 ml. of hot methanol, followed by filtration through diatomaceous earth to remove the catalyst and a small amount of unidentified material that was insoluble in the hot methanol. The alcoholic filtrate was then concentrated in vacuo and there was ultimately obtained a crude solid material which after recrystallization from a minimum amount of methanol gave 22.0 g. (82%) of pure p-amino-N-(n-decyl) benzamide, m.p. 114°–117° C.

Anal. Calc'd for $C_{17}H_{28}N_2O$: C, 73.76; H, 10.21; N, 10.14%. Found: C, 74.03; H, 9.94; N, 10.27%.

The following p-amino-N-alkylbenzamides were prepared by the same procedure and by employing the appropriate p-nitro-N-alkylbenzamide as the starting material.

p-amino-N-(n-octyl)benzamide, m.p. 118°–120° C.
p-amino-N-(n-nonyl)benzamide, m.p. 111°–114° C.
p-amino-N-(n-undecyl)benzamide, m.p. 115°–117° C.
p-amino-N-(n-dodecyl)benzamide, m.p. 121°–122° C.
p-amino-N-(n-tridecyl)benzamide, m.p. 120°–121° C.
p-amino-N-(n-pentadecyl)benzamide, m.p. 117°–119° C.
p-amino-N-(n-hexadecyl)benzamide, m.p. 117°–120° C.

p-Nitro-N-(n-heptyl)benzamide, p-nitro-N-benzylbenzamide, p-nitro-N-(β-phenylethyl)benzamide and p-nitro-N-(α-pyridyl)benzamide can be converted into the corresponding p-amino-N-monosubstituted benzamides by the foregoing procedure.

PREPARATION C

To a stirred portion of 50 ml. of thionyl chloride at room temperature was added 13.21 g. (0.10 moles) of methyl hydrogen succinate in the form of a solid divided into separate small portions. After stirring the solution under dry conditions overnight, the excess thionyl chloride was removed by vacuum evaporation. The liquid residue was distilled under reduced pressure to give 15 g. of colorless 3-carboxymethyl propionyl chloide (98%) b.p. 62°–65° at 6 torr.

Methyl hydrogen malonate, methyl hydrogen glutarate and methyl hydrogen adipate can be respectively converted into 2-carboxymethylacetyl chloride, 4-carboxymethylbutyryl chloride and 5-carboxymethylvaleryl chloride by the foregoing procedure.

PREPARATION D

To a stirred portion of 50 ml. thionyl chloride at room temperature was added 2.60 g. (0.0165 moles) of p-chlorobenzoic acid in the form of a solid divided into separate small portions. After stirring the solution under dry conditions overnight, the excess thionyl chloride was removed by vacuum evaporation which left a crude yellow residue. This residue was washed once with anhydrous ether and then dried under vacuum to give a 2.90 g. p-chlorobenzoyl chloride. It was used immediately as is in Example 5.

The following aromatic acid chlorides were prepared by the same procedure using the appropriate aromatic carboyxlic acid and used in the examples cited.

o-chlorobenzoyl chloride: Example 10
o-methoxybenzoyl chloride: Example 8
p-methoxybenzoyl chloride: Example 9
picolinyl chloride: Example 15
nicotinyl chloride: Example 13
isonicotinyl chloride: Example 14
p-carboxymethylbenzoyl chloride: Example 11

EXAMPLE I

N-(3-carboxymethylpropionyl)-p-amino-N'-(n-decyl)-benzamide

To a stirred slurry of 9.28 g. (0.034 moles) of p-amino-N-(n-decyl)benzamide in 100 ml. of dry benzene and 50 ml. of dry pyridine at room temperature was added 5.30 g. (0.035 moles) of 3-carboxymethyl propionyl chloride in 10 ml. dry benzene. Upon completion of the addition, the mixture was heated to reflux for 3 hours and then allowed to cool. It was then poured into 150 ml. of water and the resulting two phase mixture was extracted with two-200 ml. portions of methylene chloride. The combined organic solution was dried with magnesium sulfate and then suction filtered to remove the drying agent. After removal of the solvent in vacuo, a crude, solid residue was obtained which was redissolved in hot methanol. Decolorization of this methanol solution with carbon black followed by suction filtration through diatomaceous earth to remove the decolorizing agent gave after dilution with water and cooling 9.35 g. (70%) of pure N-(3-carboxymethylpropionyl)-p-amino-N'-(n-decyl)benzamide, m.p. 160°–163.5° C.

Anal. Calc'd for $C_{22}H_{34}O_4N_2$: C, 67.66; H, 8.78; N, 7.17%. Found: C, 67.85; H, 8.81; N, 7.32%.

N-(2-Carboxymethylacetyl)-p-amino-N'-(n-decyl)-benzamide, N-(4-carboxymethylbutyryl)-p-amino-N'-(n-decyl)benzamide and N-(5-carboxymethylvaleryl)-p-amino-N'-(n-decyl)benzamide can be prepared by using the appropriate acid chloride in the foregoing procedure. Other compounds which can be prepared in this manner include N-(2-carboxymethylacetyl)-p-amino-N'-(n-octyl)benzamide, N-(5-carboxyethylvaleryl)-p-amino-N'-(n-hexadecyl)benzamide, N-(4-carboxymethylbutyryl)-p-amino-N'-(β-phenylethyl)benzamide and N-(3-carboxymethylpropionyl)-p-amino-N'-(α-pyridyl)benzamide.

EXAMPLE 2

N-(3-carboxypropionyl)-p-amino-N'-(n-decyl)benzamide

To a solution of 5.76 g. (0.0147 moles) N-(3-carboxymethylpropionyl)-p-amino-N'-(n-decyl) benzamide in 250 ml. reagent methanol was added 30 ml. 5% w/w aqueous sodium hydroxide. The solution was stirred and after ca. 10 minute a precipitate formed. Stirring was continued for one hour then the slurry was poured into 200 ml. water and neutralized with one normal hydrochloric acid. The resulting precipitate was filtered and then triturated with boiling 95% ethanol. The turbid ethanol solution was cooled and the precipitate filtered to give 5.43 g. (98%) of the title compound, m.p. 300° C dec.

Anal. Calc'd for $C_{42}H_{64}O_4N_2 \cdot H_2O$: C, 65.60; H, 8.58; N, 7.23%. Found: C, 65.63; H, 8.40; N, 7.31%.

N-(2-Carboxyacetyl)-p-amino-N'-(n-decyl) benzamide, N-(4-carboxybutyryl)-p-amino-N'-(n-decyl) benzamide, N-(5-carboxyvaleryl)-p-amino-N'-(n-decyl) benzamide, N-(2-carboxyacetyl)-p-amino-N'-(n-octyl) benzamide, N-(5-carboxyvaleryl)-p-amino-N'-(n-hexadecyl) benzamide and N-(4-carboxybutyryl)-p-amino-N'-(β-phenylethyl) benzamide, can be prepared using the foregoing procedure.

EXAMPLE 3

N-(dl-2,3-diacetoxy-3-carboxymethylpropionyl)-p-amino-N'-(n-decyl)benzamide

To a stirred slurry of 8.30 g. (0.030 moles) of p-amino-N-(n-decyl)benzamide in 100 ml. of dry benzene and 50 ml. of dry pyridine at room temperature was added 8.80 g. (0.030 moles) of dl-2,3-diacetoxy-3-carboxymethyl propionyl chloride (J. Am. Chem. Soc., 63, 1655 (1941) in 10 ml. dry benzene. Upon completion of the addition, the mixture was heated to reflux for 3 hours and then allowed to cool. It was then poured into 150 ml. of water and the resulting two phase mixture was extracted with two-200 ml. portions of methylene chloride. The combined organic solution was dried with magnesium sulfate and then suction filtered to remove the drying agent. After removal of the solvent in vacuo, a crude, solid residue was obtained which was re-dissolved in hot methanol. Decolorization of this methanol solution with carbon black followed by suction filtration through diatomaceous earth to remove the decolorizing agent gave after dilution with water and cooling 2.13 g. (14%) of the title compound, m.p. 60°–63° C.

Anal. Calc'd for $C_{26}H_{38}O_8N_2$: C, 61.64; H, 7.56; N, 5.53%. Found: C, 61.71; H, 7.49; N, 5.46%.

N-(2,3,4,5-Tetraacetoxy-6-carboxymethylvaleryl)-p-amino-N'-(n-decyl)benzamide can be prepared by using the appropriate acid chloride in the foregoing procedure.

EXAMPLE 4

N-(dl-2,3-dihydroxy-3-carboxypropionyl)-p-amino-N'-(n-decyl)benzamide

To a solution of 1.12 g. (0.002 moles) N-(dl-2,3-diacetoxy-3-carboxymethylpropionyl)-p-amino-N'-decylbenzamide in 50 ml. reagent methanol was added 25 ml. 5% w/w aqueous sodium hydroxide. The solution was stirred and after ca. 10 minutes, a precipitate formed. Stirring was continued for 1 hour and then to the slurry was added 25 ml. of chloroform and resulting mixture was neutralized with one normal hydrochloric acid. The resulting precipitate was filtered and then triturated with boiling 95% ethanol. The hot ethanol solution was cooled and the precipitate filtered to give 0.84 g. (98% yield) of the title compound, m.p. 254° C dec.

Anal. Calc'd for $C_{42}H_{64}O_{12}N_{4.3}H_2O$: C, 57.92; H, 7.10; N, 6.43%. Found: C, 57.88; H, 7.06; N, 6.39%.

EXAMPLE 5

N-(p'-chlorobenzoyl)-p'-amino-N'-(n-decyl) benzamide

To a stirred slurry of 4.15 g. (0.015 moles) of p-amino-N-(n-decyl) benzamide in 50 ml. of dry benzene and 5 ml. of dry pyridine at room temperature was added a slurry of 2.89 g. (0.017 moles) of p-chlorobenzoyl chloride in 10 ml. of dry benzene. After the addition was complete, the mixture was heated to reflux for 6 hours and then allowed to cool. The entire mixture was then poured into 150 ml. of water which resulted in the formation of a solid precipitate. After isolation of this precipitate by suction filtration, it was recrystallized from 95% ethanol to give 4.13 g. of the title compound, m.p. 240°–242° C.

Anal. Calc'd for $C_{24}H_{31}O_2N_2Cl$: C, 69.47; H, 7.53; N, 6.75; Cl, 8.54%. Found: C, 69.18; H, 7.55; N, 6.69; Cl, 8.52%.

Using the foregoing procedure, N-(benzoyl)-p-amino-N'-(n-octadecyl) benzamide, N-(benzoyl)-p-amino-N'-(n-heptyl) benzamide, N-(benzoyl)-p-amino-N'-(n-undecyl) benzamide, N-(m-trifluoromethylbenzoyl)-p-amino-N'-(benzyl) benzamide, N-(α-naphthoyl)-p-amino-N'-(n-heptyl) benzamide, N-(α-thionyl)-p-amino-N'-(benzyl) benzamide, N-(p'-phenylbenzoyl)-p-amino-N'-(α-pyridyl) benzamide and N-(p'-methoxybenzoyl)-p-amino-N'-(α-pyridyl) benzamide can be prepared by employing the appropriate acid chloride and aminobenzamide.

EXAMPLES 6 – 11

N-(aroyl)-p-amino-N'-(n-decyl)benzamides

The following compounds were prepared using the procedure described in Example 5 except that the appropriate aromatic acid chloride was used in place of p-chlorobenzoyl chloride.

| Example No. | Aroyl Group | m.p., °C. | Analysis Calc'd | Found |
|---|---|---|---|---|
| 6 | benzoyl | 213–214 | C, 75.75 | C, 75.53 |
|   |   |   | H, 8.48 | H, 8.51 |
|   |   |   | N, 7.36 | N, 7.31 |
| 7 | 2-phenylacetyl | 199–200 | C, 76.10 | C, 75.97 |
|   |   |   | H, 8.69 | H, 8.54 |
|   |   |   | N, 7.10 | N, 6.87 |
| 8 | o'-methoxybenzoyl | 154–155 | C, 73.14 | C, 73.31 |
|   |   |   | H, 8.35 | H, 8.28 |
|   |   |   | N, 6.82 | N, 6.74 |
| 9 | p'-methoxybenzoyl | 231–232 | C, 73.14 | C, 73.03 |
|   |   |   | H, 8.35 | H, 8.08 |
|   |   |   | N, 6.82 | N, 6.49 |
| 10 | o'-chlorobenzoyl | 144–146 | C, 69.46 | C, 69.44 |
|   |   |   | H, 7.53 | H, 7.46 |
|   |   |   | N, 6.75 | N, 6.54 |
| 11 | p'-carboxymethyl-benzoyl | 245–265 | C, 71.20 | C, 71.02 |
|   |   |   | H, 7.82 | H, 7.88 |
|   |   |   | N, 6.39 | N, 6.49 |

EXAMPLE 12

N-(benzoyl)-p-amino-N'-(n-tridecyl)benzamide

To a stirred slurry of 3.18 g., (0.010 moles) of p-amino-N-(n-tridecyl)benzamide in 50 ml. of dry benzene and 5 ml. of dry pyridine at room temperature was added a solution of 1.55 g. (0.010 moles) of benzoyl chloride in 10 ml. of dry benzene. After the addition was complete, the mixture was heated to reflux for 6 hours and then allowed to cool. The entire mixture was then poured into 150 ml. of water which resulted in the formation of a solid precipitate. After isolation of this precipitate by suction filtration, it was re-crystallized from 95% ethanol to give 3.79 g. (90%) of the title compound, m.p. 207°–208° C.

Anal. Calc'd for $C_{25}H_{38}O_2N_2$: C, 76.73; H, 9.06; N, 6.63%. Found: C, 76.46; H, 9.10; N, 6.50%.

EXAMPLES 13 – 17

N-aroyl-p-amino-N'-(n-tridecyl) benzamide

The following compounds were prepared using the procedure described in Example 12 except that the appropriate aromatic acid chloride was used in place of benzoyl chloride.

| Example No. | Aroyl Group | m.p., °C. | Analysis Calc'd% | Found% |
|---|---|---|---|---|
| 13 | nicotinyl | 194–195 | C, 73.72 | C, 73.74 |
|   |   |   | H, 8.80 | H, 8.98 |
|   |   |   | N, 9.92 | N, 9.72 |
| 14 | isonicotinyl | 202–203 | C, 73.72 | C, 73.47 |
|   |   |   | H, 8.80 | H, 8.89 |
|   |   |   | N, 9.92 | N, 9.82 |
| 15 | picolinyl | 160° dec | C, 73.72 | C, 72.37 |
|   |   |   | H, 8.80 | H, 8.75 |
|   |   |   | N, 9.92 | N, 10.30 |
| 16 | 4-hydroxynicotinyl | 314° dec | C, 71.04 | C, 70.84 |
|   |   |   | H, 8.48 | H, 8.50 |
|   |   |   | N, 9.56 | N, 9.46 |
| 17 | 2-(o'-carboxyphenyl)acetyl | 210–212 | C, 72.47 | C, 72.12 |
|   |   |   | H, 8.39 | H, 8.57 |
|   |   |   | N, 5.80 | N, 6.00 |

EXAMPLE 18

N-(acetyl)-p-amino-N'-(n-decyl) benzamide

To a stirred slurry of 5.00 g. (0.018 moles) of p-amino-N-(n-decyl) benzamide in 50 ml. of acetic anhydride at room temperature was slowly added 5 ml. concentrated, reagent grade sulfuric acid. Upon the addition of the $H_2SO_4$, the solid suspended in the acetic anhydride dissolved and the resulting solution was stirred at room temperature for one hour. It was then poured onto a stirring portion of 200 g. ice in 20 ml. water which resulted in the formation of a white precipitate. After isolation of this precipitate by suction filtration, it was recrystallized from ethanol to give 3.53 g. of the title compound, m.p. 166°–167° C.

Anal. Calc'd for $C_{19}H_{30}O_2N_2$: C, 71.66; H, 9.50; N, 8.80%. Found: C, 71.48; H, 9.73; N, 8.65%.

EXAMPLE 19

N-(acetyl)-p-amino-N'-(n-tridecyl) benzamide

The title compound, m.p. 168°–169° C, was prepared using the same procedure described in Example 18 except that p-amino-N'-(n-tridecyl) benzamide was used as the starting material.

Using the procedure of Example 18, N-(propionyl)-p-amino-N'-(benzyl) benzamide, N-(butyryl)-p-amino-N'-(β-phenylethyl) benzamide, N-(valeryl)-p-amino-N'-(octyl) benzamide and N-(propionyl)-p-amino-N'-(n-hexadecyl) benzamide can be prepared by employing the appropriate anhydride and aminobenzamide.

EXAMPLE 20

N-(phenoxyformyl)-p-amino-N'-(n-tridecyl) benzamide

To a stirred slurry of 3.18 g. (0.10 moles) of p-amino-N-(n-tridecyl) benzamide in 50 ml. of dry benzene and 10 ml. of dry pyridine at room temperature was added a solution of 2.35 g. (0.015 moles) of phenylchloroformate in 10 ml. of dry benzene. After the addition was complete, the mixture was heated to reflux overnight and then allowed to cool. The entire mixture was then poured into 150 ml. of water and extracted with two- 200 ml. portions of ethyl acetate. The combined organic solution was dried with magnesium sulfate and then suction filtered to remove the drying agent. After removal of the solvent in vacuo, a crude, solid residue was obtained which was recrystallized from benzene to give 1.72 g. of the title compound, dec. 200° C.

Anal. Calc'd for $C_{27}H_{38}O_3N_2$: C, 73.94; H, 8.73; N, 6.39%. Found: C, 73.70; H, 9.07; N, 6.74%.

Using the procedure of Example 20, N-(phenoxyformyl)-p-amino-N'-(β-phenylethyl) benzamide and N-(phenoxyformyl)-p-N'-(α-pyridyl) benzamide and N-(phenoxyformyl)-p-amino-N'-(benzyl) benzamide can be prepared by employing the appropriate aminobenzamide.

EXAMPLE 21

N-(3-sulfonoxypropionyl)-p-amino-N'-(n-decyl) benzamide

To a stirred slurry of 5.52 g. (0.020 moles) of p-amino-N-(n-decyl) benzamide in 75 ml. of dry methylene chloride at room temperature was added 2.72 g. (0.020 moles) of 3-sulfopropionic anhydride in the form of a solid divided into separate small portions. Upon completion of the addition, the mixture was allowed to stir overnight during which time a precipitate formed. Filtration of this precipitate followed by recrystallization from ethanol gave 6.90 g. of the impure title compound, m.p. 235°–236° C.

IR, (KBr pellet), 3.00, 3.55, 5.80, 6.10, 8.40, 8.55, 9.65 u.

Using the foregoing procedure, N-(3-sulfonoxypropionyl)-p-amino-N'-(tridecyl) benzamide, N-(3-sulfonoxypropionyl)-p-amino-N'-(benzyl) benzamide, N-(3-sulfonoxypropionyl-p-amino-N'-(hexadecyl) benzamide, N-(4-sulfonoxybutyryl)-p-amino-N'-(decyl) benzamide, N-(5-sulfonoxyvaleryl)-p-amino-N'-(decyl) benzamide and N-(4-sulfonoxybutyryl)-p-amino-N'-(benzyl) benzamide can be prepared by employing the appropriate sulfoaliphatic anhydride and aminobenzamide.

What is claimed is:

1. A compound of the formula

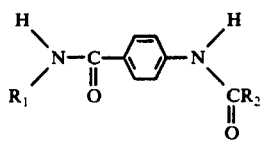

wherein:
$R_1$ is selected from the group consisting of n-alkyl having from seven to eighteen carbon atoms, phenyl, benzyl and phenylethyl,
$R_2$ is selected from the group consisting of —$(CH_2)_n$-$CO_2R_3$, —$(CHOR_4)_nCO_2R_3$ and

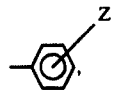

said Z substituent being —$(CH_2)_uCO_2R_3$,
$R_3$ is hydrogen or alkyl having from one to five carbon atoms,
$R_4$ is hydrogen or acetyl;
$n$ is an integer from one to four;
$u$ is 0 or an integer from one to two; and the alkali, alkaline earth and ammonium salts of those compounds having at least one carboxylate group.

2. A compound of claim 1 wherein $R_1$ is n-alkyl.

3. A compound of claim 2 wherein $R_2$ is

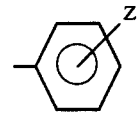

4. A compound of claim 2 wherein $R_2$ is —$(CH_2)_n$-$CO_2R_3$.

5. The compound of claim 4 wherein $R_1$ is n-decyl and $R_2$ is —$(CH_2)_2CO_2H$.

6. A composition for peptic ulcer control comprising an effective amount of a compound of claim 1 in admixture with a pharmaceutically acceptable carrier.

7. A method of controlling peptic ulcers in an animal which comprises intraperitoneally or orally administering to an animal in need of such control a peptic ulcer controlling amount of a compound of claim 1.

8. A method of claim 7 wherein $R_1$ is n-alkyl and $R_2$ is

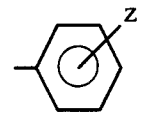

9. A method of claim 7 wherein $R_1$ is n-alkyl and $R_2$ is —$(CH_2)_nCO_2R_3$.

10. A method of claim 9 wherein $R_1$ is n-decyl and $R_2$ is —$(CH_2)_2CO_2H$.

* * * * *